US008063901B2

(12) United States Patent
Paladini et al.

(10) Patent No.: US 8,063,901 B2
(45) Date of Patent: Nov. 22, 2011

(54) METHOD AND APPARATUS FOR EFFICIENT CLIENT-SERVER VISUALIZATION OF MULTI-DIMENSIONAL DATA

(75) Inventors: Gianluca Paladini, Skillman, NJ (US); Mathia Scucchiari, Padua (IT); Thomas Moeller, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 775 days.

(21) Appl. No.: 12/157,082

(22) Filed: Jun. 6, 2008

(65) Prior Publication Data

US 2009/0016641 A1  Jan. 15, 2009

Related U.S. Application Data

(60) Provisional application No. 60/944,858, filed on Jun. 19, 2007.

(51) Int. Cl.
*G06K 9/40* (2006.01)
*G06K 9/46* (2006.01)
*G06K 9/64* (2006.01)
*G06T 17/00* (2006.01)

(52) U.S. Cl. ......... 345/424; 382/240; 382/248; 382/278

(58) Field of Classification Search .................. 348/163, 348/419, 420, 428; 382/240; 715/856, 866; 345/428

See application file for complete search history.

(56) References Cited

U.S. PATENT DOCUMENTS

| 6,208,347 | B1 | 3/2001 | Migdal et al. |
| 6,750,845 | B2* | 6/2004 | Hopper ......................... 345/156 |
| 7,042,454 | B1 | 5/2006 | Seligman |
| 2004/0179744 | A1 | 9/2004 | Chang et al. |
| 2007/0115282 | A1* | 5/2007 | Turner et al. .................. 345/424 |

OTHER PUBLICATIONS

Yaniv Zigel, Arnon Cohen, and Amos Katz, "ECG Signal Compression Using Analysis by Synthesis Coding", Oct. 2000, IEEE Transactions on Biomedical Engineering, vol. 47, No. 10, pp. 1308-1316.*
Engel, K., et al., "Combining Local and Remote Visualization Techniques for Interactive Volume Rendering in Medical Applications", Proc. IEEE Visualization, 2000, 449-452.
Levoy, M., "Display of Surfaces from Volume Data", IEEE Computer Graphics and Applications, 1988, 29-37.

* cited by examiner

*Primary Examiner* — Kee M Tung
*Assistant Examiner* — Sing-Wai Wu

(57) ABSTRACT

In response to a request from a client, a server for volume rendering loads a volume dataset from a storage archive, creates a low resolution sub-sampled copy of such volume dataset and transmits it to a client. In response to subsequent requests from the client, the server for volume rendering renders a high quality image of the full resolution volume dataset and renders a low quality image of the sub-sampled copy of the volume dataset, then generates a pixel mask or a hybrid pixel mask indicative of a difference between the high quality image and the low quality image and transmits such pixel mask to the client. The client receives from the server the pixel mask and computes a high quality image based at least in part on the pixel mask and on a selective rendering of its local low resolution sub-sampled copy of the volume dataset.

23 Claims, 8 Drawing Sheets

METHOD AND APPARATUS FOR EFFICIENT CLIENT-SERVER VISUALIZATION OF MULTI-DIMENSIONAL DATA

This application claims the benefit of U.S. Provisional Application No. 60/944,858 filed Jun. 19, 2007 which is incorporated herein by reference.

BACKGROUND OF THE INVENTION

The present invention relates generally to visualization of three dimensional and four dimensional data and more particularly to client-server architecture for visualization of three dimensional and four dimensional data.

Visualization of multi-dimensional data is generally produced as a rendered volume image. Volume rendering is the process of generating a two dimensional (2D) image from a three dimensional (3D) dataset (e.g., a volume comprised of a stack of 2D images) as it would appear from a specified location with specified rendering parameters (e.g., shading, type of projection, etc.). One method of volume rendering is referred to as ray casting as described in Levoy, "Display of Surfaces from Volume Data", IEEE Computer Graphics and Applications, Vol. 8, No. 3, May 1988, pp. 29-37.

The primary technical obstacle to implementing a system for interactive volume rendering is quickly, efficiently, and locally processing large amounts of data required to render each frame. The large data volume problem is exacerbated by modern medical imaging equipment, which can themselves acquire large amounts of data. For example, the Siemens Somatom Sensation 64 CT scanner, which can acquire slices of 0.33 mm in thickness, five thousand or more slices may be required for a full body scan. The amount of memory required to store such a large volume of data, as well as the processing performance needed to render it, exceeds the capabilities for typical local processors (e.g., desktop personal computers (PCs), laptops, etc.).

A common approach to circumvent this problem is to utilize a client-server architecture, where a fast server machine with substantial memory and processing power is used to generate a volume rendered image, which is then transmitted over a network to a client machine (e.g., client PC, etc.) where the volume rendered image is displayed. In some instances, a thin client is utilized. That is, the client machine does not require any special processing power and is only used to display images which are entirely computed at the server. Such a thin client architecture is described in U.S. Pat. No. 6,683,933 entitled "Three-dimensional image display device in network" (Saito). One problem with this approach is that it requires a large amount of images to be transmitted from the server to the client. Every time a user interacts with a 3D volume's viewing parameters (e.g., orientation, rotation, translation scaling, color, opacity, shading, etc.) using a pointing device such as a mouse, the client notifies the server about those changes and the server renders a new image and transmits the new image to the client. Using the client-server architecture in such a fashion can be costly and slow due to the large amount of updates.

A common approach to mitigate these problems is to use data compression techniques. The use of compression techniques is limited because, in a clinical setting, the images displayed at the client have to preserve the original diagnostic quality. That is, the integrity of the original image data should not be potentially compromised by the use of lossy compression algorithms. Examples of lossless techniques to transmit compressed images over a network are described in U.S. Pat. No. 4,751,587 entitled "Image recording and reproducing apparatus using differential data compression and expansion techniques" (Asahina) and in U.S. Pat. No. 6,925,117 entitled "Data transmission apparatus, method and program, data reception apparatus and method, and data transmission and reception system, using differential data" (Kamisuwa). These methods rely on differential compression. In differential compression, new data is subtracted from reference data. The resulting difference is compressed and transmitted from the server to the client and the client expands the difference data and subtracts it from the reference data, thereby obtaining the new data. One restriction of differential compression is that the reference data needs to reside both on the client and the server. Even with the use of differential compression techniques to reduce the required transmission bandwidth, it is difficult to achieve interactive performance for multiple clients. In present practice, ten or more rendered frames per second are typically needed to be transmitted over the network for each client. If there are numerous clients connected to a server, the network bandwidth is a significant bottleneck.

Another approach to minimize the amount of data transferred from the server to the client is to use a hybrid combination of local and remote volume rendering, (e.g., a smart client) as described by Engel et al., "Combining local and remote visualization techniques for interactive volume rendering in medical applications", Proceedings of IEEE Visualization '00. Piscataway, N.J.: Institute of Electrical and Electronics Engineers, 2000; 449-452. In the smart client architecture, the application logic and processing resides on the server and the client has the ability to do local processing as well. The server first transfers a low-resolution, sub-sampled copy of the volume data to the client. When the user interacts with the volume, the smart client performs volume rendering locally using the sub-sampled copy of the volume, without needing to request any work to be performed by the server. Upon completion of user interaction (e.g., the user stops moving the mouse and/or releases the mouse button, etc.), the smart client sends a request to the server to render one image and send it over the network. While the number of images rendered by the server is greatly reduced in such an approach and the interactive performance is improved, the images rendered locally by the smart client during interaction are computed using low resolution sub-sampled data and the resulting images do not preserve the original diagnostic quality.

Accordingly, systems and methods are required that can solve all the aforementioned issues related to thin client, smart client, and differential compression techniques and can provide a solution that has fast performance during interactive volume rendering on the client while visualizing images of full diagnostic quality and minimizing the amount of network bandwidth needed to have a server transmit images to multiple clients.

BRIEF SUMMARY OF THE INVENTION

The present invention relates generally to visualization of three dimensional and four dimensional data and more particularly to client-server architecture for visualization of three dimensional and four dimensional data. In response to a request from a client, a server for volume rendering loads a volume dataset from a storage archive, creates a low resolution sub-sampled copy of such volume dataset and transmits it to the client. The sub-sampled copy of the full resolution volume dataset may be encoded and compressed before transmission. In response to subsequent requests from the client, the server for volume rendering renders a high quality image of the full resolution volume dataset and renders a low quality image of the sub-sampled copy of the volume dataset, then generates a pixel mask or a hybrid pixel mask indicative of a difference between the high quality image and the low quality image and transmits such pixel mask to the client.

The client receives from the server the pixel mask and computes a high quality image based at least in part on the pixel mask and on a selective rendering of its local low-resolution sub-sampled copy of the volume dataset.

These and other advantages of the invention will be apparent to those of ordinary skill in the art by reference to the following detailed description and the accompanying drawings.

DETAILED DESCRIPTION

One embodiment of the present invention includes a system for remotely rendering large 3D and 4D data sets over a low bandwidth network with efficient interactive performance and efficient full fidelity visualization on conventional PC-based client hardware. Such a system may be applied to various volume rendering techniques, including direct volume rendering, maximum intensity projection, and multi-planar reformatting.

Figure 1:
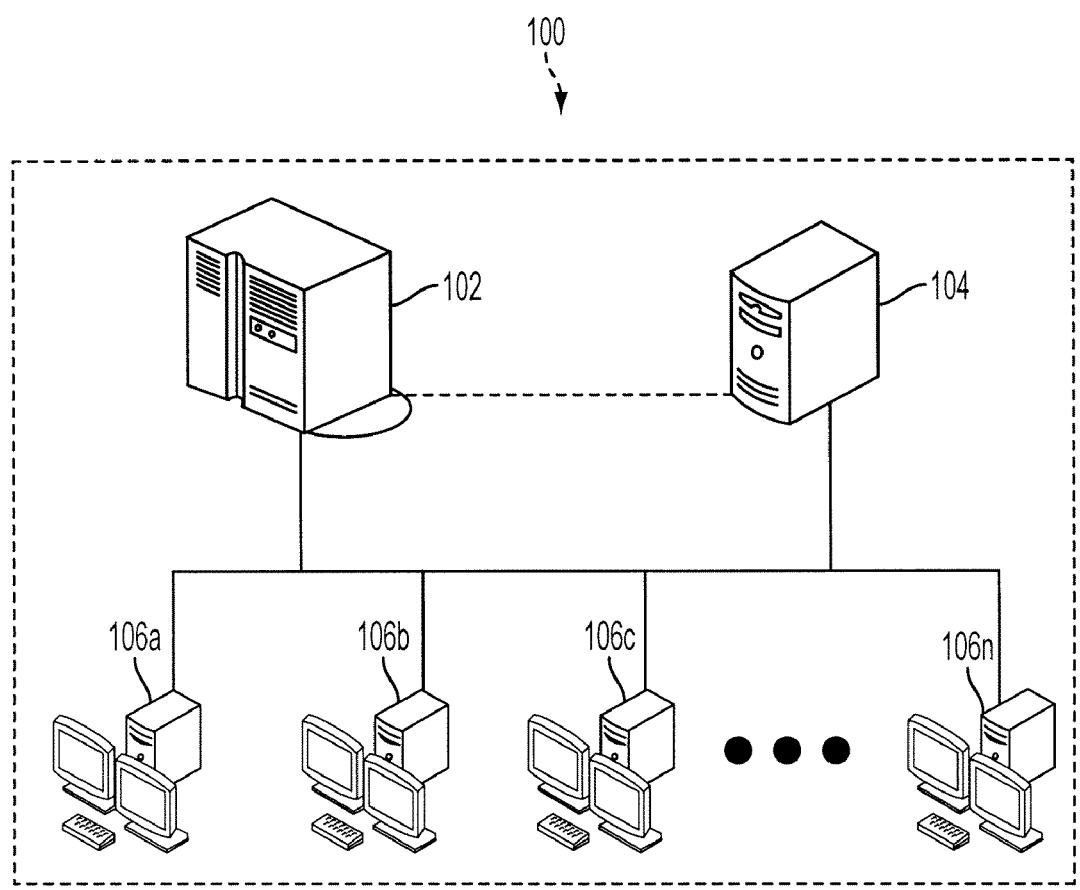
FIG. 1 depicts a volume rendering system according to an embodiment of the present invention.

FIG. 1 depicts a volume rendering system 100 according to an embodiment of the present invention. Volume rendering system 100 includes a Picture Archiving and Communication System (PACS) 102 coupled to one or more processing servers 104. The PACS 102 and processing servers 104 are each coupled to one or more clients 106a-na, 106b, 106c, . . . , 106n.

PACS 102 may be one or more computers or networks dedicated to the storage, retrieval, distribution, and presentation of images as is known. In at least one embodiment PACS 102 may be a server and/or scan devices capable of transmitting image data, such as a computed tomography (CT) or magnetic resonance (MR) scanner. In some embodiments, these images are stored in an independent format, such as Digital Imaging and Communications in Medicine (DICOM) for medical images.

Figure 2:
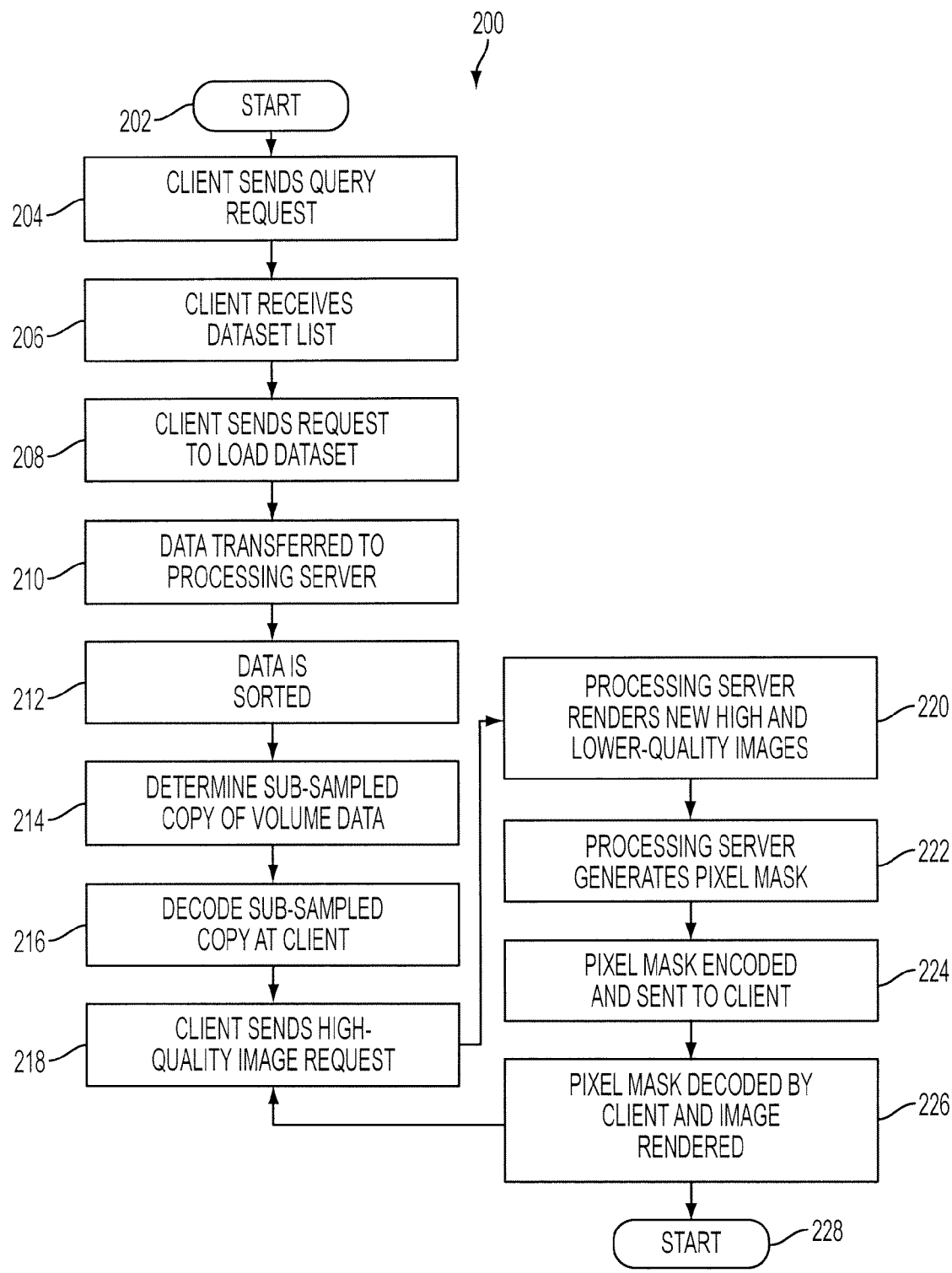
FIG. 2 is a flowchart of a method of volume rendering according to an embodiment of the present invention.

Processing server 104 is preferably a high-performance machine capable of rendering large volume data at high speed and configured to perform the various other functions described herein, especially with respect to FIG. 2. An exemplary computer 800 described below with respect to FIG. 8 may be used as a processing server 104. In at least one embodiment, processing server 104 includes a central processor and a large amount of memory and data storage. In the same or alternative embodiments, processing server 104 includes additional high-speed computing devices, high-capacity memory connected to a high-speed bus, and/or dedicated processing boards based on processors such as digital signal processing (DSP), graphics processing unit (GPU), or field-programmable gate array (FPGA) chips. Though depicted in FIG. 1 as a single processing server 104, it should be understood that multiple processing servers 104 may be coupled to the PACS 102 and clients 106a-n. In this way, the volume rendering system 100 and processing server architecture is scalable in order to be able to support a large number of clients 106a-n and has the ability to be expanded in a cluster-based configuration where multiple processing server 104 nodes are connected together and work in parallel. Processing server 104 may be coupled to PACS 102 by a high-speed network connection and to clients 106a-n by a low to medium speed connection. In at least one embodiment, processing server 104 and PACS 102 may be implemented as a single unit. That is, processing server 104 and PACS 102 may be combined to share functionality and processing resources.

Clients 106a-n may be any appropriate computer, client, or computer product configured to perform the various functions described herein, especially with respect to FIG. 2. An exemplary computer 800 described below with respect to FIG. 8 may be used as a client 106. Clients 106a-n may be computer workstations as are known. In some embodiments clients 106a-n may be or may have the capabilities found in conventional personal desktop computers, laptops, and the like.

FIG. 2 is a flowchart of a method 200 of volume rendering according to an embodiment of the present invention. Method 200 may be implemented by any appropriate combination of components of volume rendering system 100. The method begins at step 202.

In step 204, a client 106 sends a query request to PACS 102. This may be a request to acquire a list of volume datasets available for loading, where each dataset is composed by a series of images (e.g., CT slices, MR slices, etc.). In some embodiments, the dataset list can be viewed at the client 106, using an appropriate user interface (UI), in the form of a "Worklist" that displays datasets scheduled to be viewed at a specific time. In the same or alternative embodiments, the dataset list may be organized based on search parameters specified by a user at client 106 through a patient-specific UI. That is, a UI at a client 106 may be pre-configured and/or configurable to display image information requested by a user.

In step 206, PACS 102 sends the requested dataset list to the client 106. The dataset list may be displayed to a user at client 106 via one or more UIs as described above.

In step 208, the client 106 sends a request to PACS 102 to load a dataset from the PACS 102 to processing server 104. This request may be in response to a user selection of one or more datasets from the received dataset list in step 206.

In step 210, processing server 104 requests volume data based on the selected dataset from PACS 102 and the requested data is transferred to the processing server 104. As discussed above, in some embodiments PACS 102 and processing server 104 may be combined as a PACS/processing server unit (not shown). In such embodiments, transfer of volume data and/or any other appropriate information between a client 106 and PACS 102 and/or processing server 104 or between the PACS 102 and the processing server 104, as discussed especially with respect to method steps 206-210, may be consolidated in the PACS/processing server unit.

In step 212, the volume data transferred to the processing server 104 in step 210 is sorted. The data sort may be into any appropriate order such as a user-determined order. In at least one embodiment, volume data (e.g., slices, images, etc.) is sorted by a position along a Z axis. In the same or alternative embodiments, multiple volumes may be sorted based on their acquisition time in a 4D sequence.

In step 214, a sub-sampled copy of the volume data is determined. In at least one embodiment, the determination of a sub-sampled copy of the volume data includes computing a sub-sampled copy and compressing the computed sub-sampled copy into a low resolution volume dataset with a small memory footprint. That is, the sub-sampled copy is a lower resolution version of the full resolution volume dataset and, especially when compressed, requires less memory to store and uses less bandwidth in transmission. The sub-sampled copy of the volume data is then encoded. In some embodiments, the sub-sampled copy of the volume data is encoded with lossless compression methods such as Huffman Encoding, Run-Length encoding, etc. In alternative embodiments, the sub-sampled copy of the volume data is encoded with lossy compression methods such as Joint Photographic Experts Group (JPEG) compression or the like.

In step 216, the compressed and encoded sub-sampled copy of the volume data is sent from processing server 104 to client 106, where it is decoded.

In step 218, the client 106 sends a request for a high-quality image to the processing server 104 along with information about new viewing parameters as described above. That is, the client 106 initiates a request to render a high-quality image based on one or more user inputs.

In step 220, processing server 104 renders a new high-quality image using the full resolution high-quality volume data. Processing server 104 also renders a new lower-quality image using the lower resolution sub-sampled volume determined in step 214.

In step 222, processing server 104 generates a pixel mask based on the new high-quality image and the new lower-quality image. In at least one embodiment, the pixel mask is a hybrid combination of pixel flags and pixel values known as a hybrid pixel mask. In such embodiments, every pixel of the hybrid pixel mask having a zero value indicates that the high-quality and lower-quality images had the same pixel value, while every pixel in the hybrid pixel mask having a value not equal to zero contains the pixel value corresponding to the high-quality image. Generation of a hybrid pixel mask is discussed in further detail below with respect to FIGS. 3 and 4.

In step 224, the pixel mask is encoded by processing server 104. Encoding may be accomplished with any appropriate lossless compression methods, such as Huffman Encoding or Run-Length encoding. The pixel mask is then sent to the client 106 in response to the high-quality rendering request in step 218.

Each time a new high quality image needs to be rendered and displayed on at a client 106, method steps 218-224 may be repeated.

In step 226, the client 106 decodes the compressed pixel mask, and then determines (e.g., generates, computes, etc.) a new high-quality image at the client by selectively rendering from the sub-sampled volume data only a subset of image pixels flagged with a zero value in the pixel mask. The remaining pixels values are merged into the final result from the pixel mask through an exclusive disjunction logical operation (XOR). In this way, client 106 may generate a new high-quality image.

The use of a pixel mask significantly reduces the number of computations needed by a client 106 to perform volume rendering of the local sub-sampled volume selectively. Client 106 determines, based on the pixel mask, which pixels should or should not be rendered and is thus not required to compute a full reference image as is typically used in differential compression. An exemplary hybrid pixel mask generation is shown in FIG. 3 and FIG. 4 depicts an example of resulting pixel values in a hybrid pixel mask.

The method ends at step 228.

Figure 3:
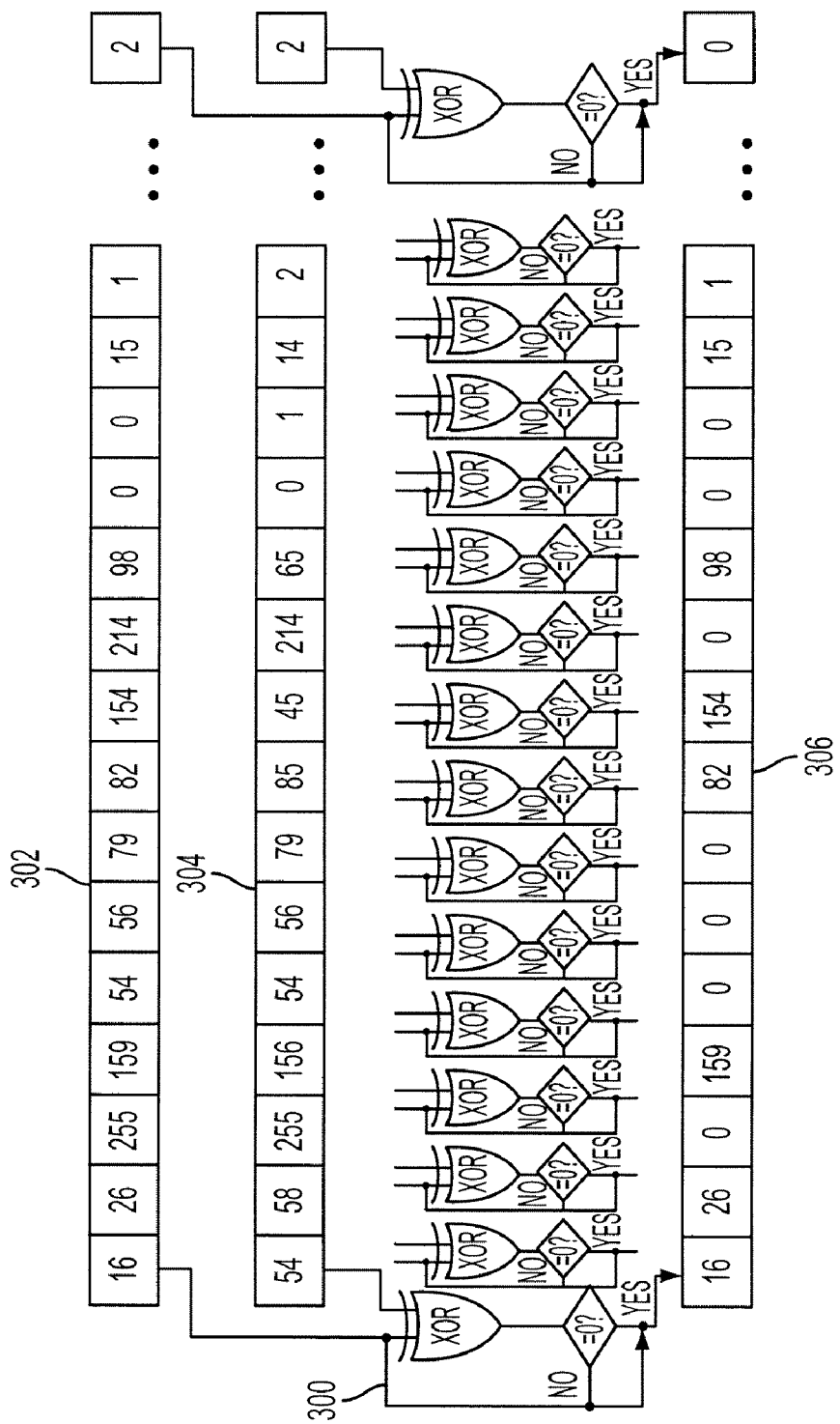
FIG. 3 depicts the use of an XOR logical operation to generate a hybrid pixel mask.

FIG. 3 depicts the use of an XOR logical operation 300 to generate (e.g., form, compute, etc.) a hybrid pixel mask. Data values 302 of a rendered reference dataset (e.g., a dataset originally acquired at PACS 102, etc.) are compared with data values 304 of a rendered sub-sampled dataset (e.g., the dataset determined in step 214 of method 200) with the XOR operation 300. Zero values resulting from the XOR operation 300 indicate pixel values that are identical in the high quality and low quality rendered images and are stored as zero values directly in the pixel mask. For non-zero values resulting from the XOR operation 300, the original pixel values from the high-quality image are stored in the pixel mask.

Figure 4:
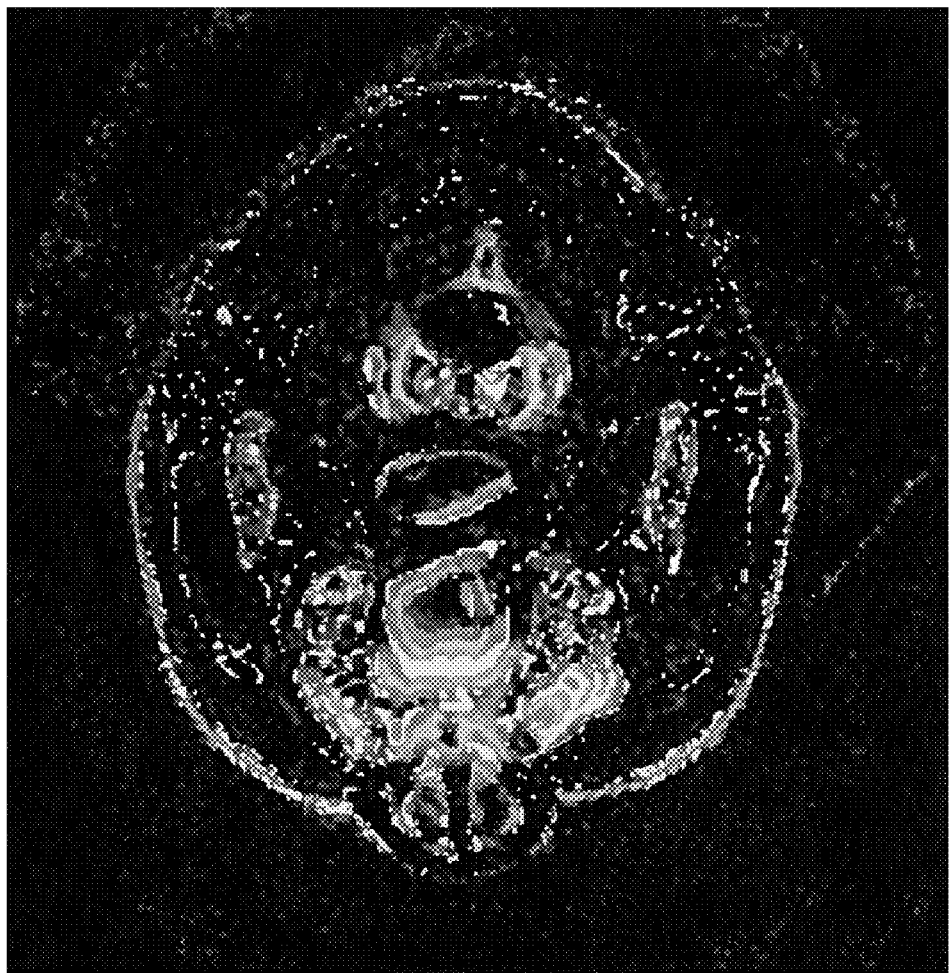
FIG. 4 depicts an exemplary image generated from pixel values in a hybrid pixel mask.

FIG. 4 depicts an exemplary image 400 generated from pixel values in a hybrid pixel mask. For example, the image 400 may be generated from the data values 306 of the hybrid pixel mask as discussed above with respect to FIG. 3. Due to the similarity between the high-quality and low-quality images, many pixels may be encoded as zero values that can be easily compressed with lossless compression methods such as Huffman Encoding, Run-Length encoding, etc.

Figure 5:
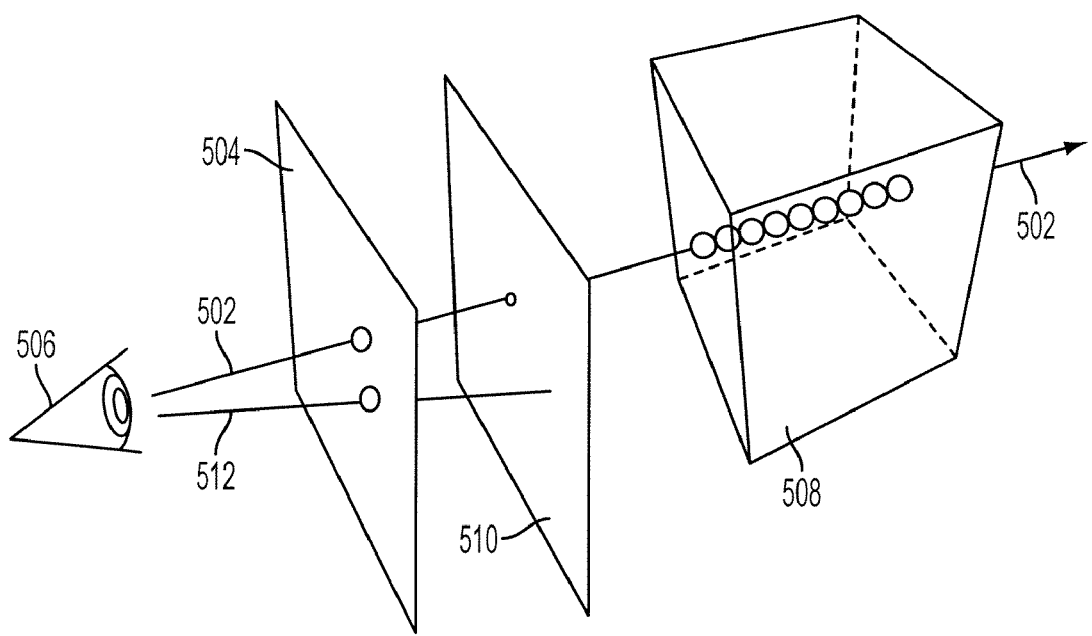
FIG. 5 depicts rendering of an image using a hybrid bit mask.

FIG. 5 depicts rendering of an image using a hybrid bit mask (e.g., the hybrid bit mask determined as in FIG. 3) as in method step 226 of method 200. A ray 502 is cast though pixels in the image plane 504 from the viewing origin 506 to the volume 508 to be rendered. Samples are computed along ray 502 that are accumulated according to various rendering techniques (e.g., alpha blending, maximum intensity projection, minimum intensity projection, etc.).

Each computed sample is trilinearly interpolated, requiring a considerable amount of computations. Even more computations are needed if the voxels are to be shaded since a gradient vector has to be computed and a shading operation (such as Phong shading) has to be computed for each voxel. Use of the inventive hybrid pixel mask 510 (e.g., hybrid pixel masks discussed above with respect to FIGS. 2-4) reduces the amount of processing required to compute a volume rendered image at a client 106 by selectively flagging the pixels through which a ray should be cast. Accordingly, only pixels that had the same value in the high-quality and low-quality images at processing server 104, and are thereby flagged as zero values in the pixel mask, need to be ray cast at the requesting client 106. As such, a ray 512 that is not cast is not sent to rendered volume 508 and the lengthy processing time associated with the interpolation of samples along such a ray is avoided.

In imaging embodiments employing Multi-Planar Reformatting (MPR) (e.g., reconstruction of images in the coronal and sagittal planes in conjunction with the original axial dataset), the selective rendering is implemented by casting rays 502 along each row of pixels in the image plane. In such embodiments, since ray samples correspond to pixels in the image plane, the hybrid pixel mask flags which samples along the ray should be computed.

Figure 6:
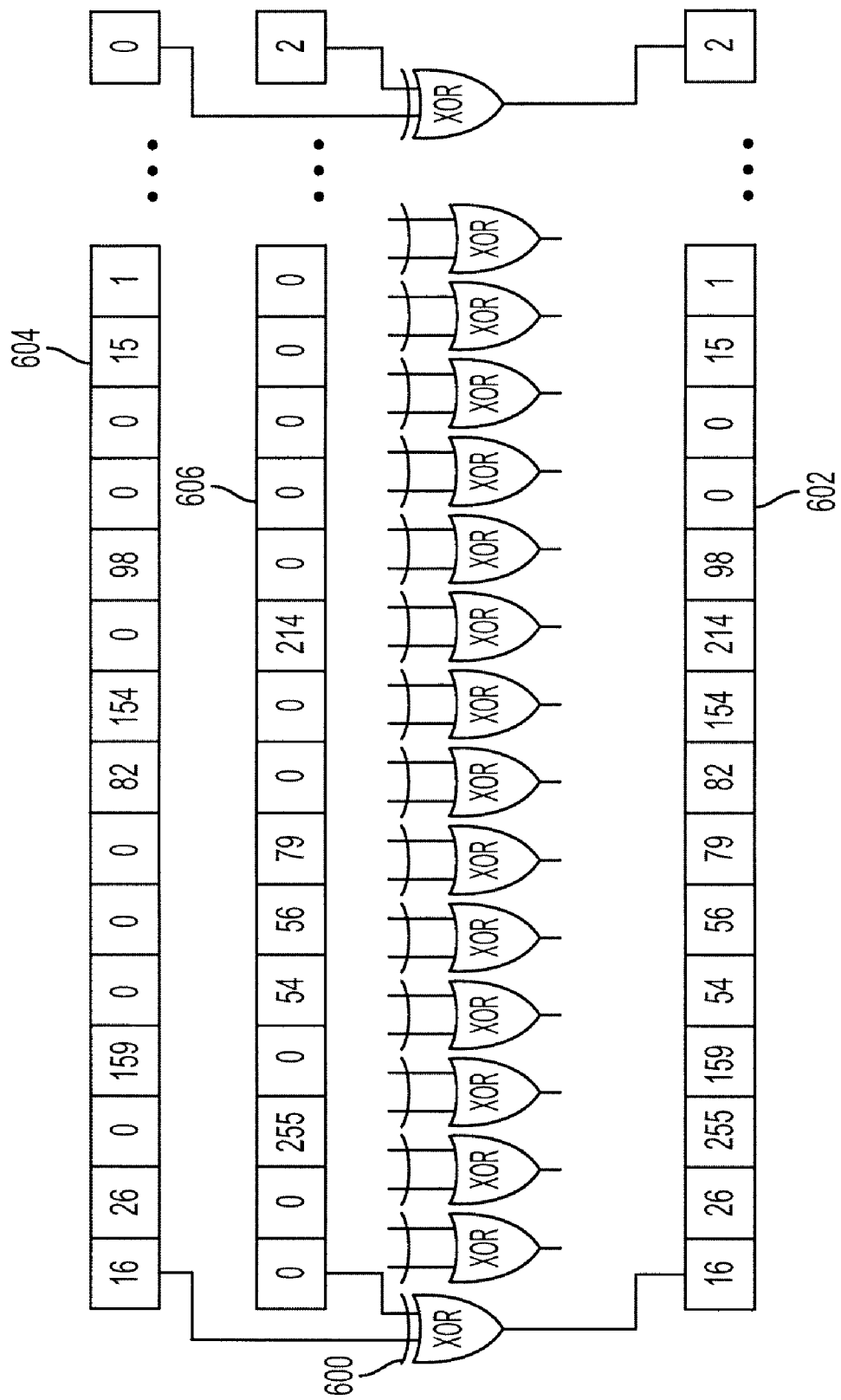
FIG. 6 depicts the use of an XOR logical operation to combine a hybrid pixel mask with a selectively rendered image.

Further to method step 226 above, after selective pixel rendering computation is completed, the client 106 executes a final refinement pass in order to generate the full quality image to be drawn on the screen. This operation includes a logical XOR between the hybrid pixel mask and the local image buffer computed using selective rendering. FIG. 6 shows an example of such operation.

FIG. 6 depicts the use of an XOR logical operation 600 to refine (e.g., generate, form, compute, etc.) pixel values 602 for a high-quality image to be displayed by the client 106. Non-zero pixel values 604 of the hybrid pixel mask are merged with non-zero pixel values 606 of a selectively rendered image from client 106 with the XOR operation 600. In this way, a final high-quality image 602 is formed.

Figure 7:
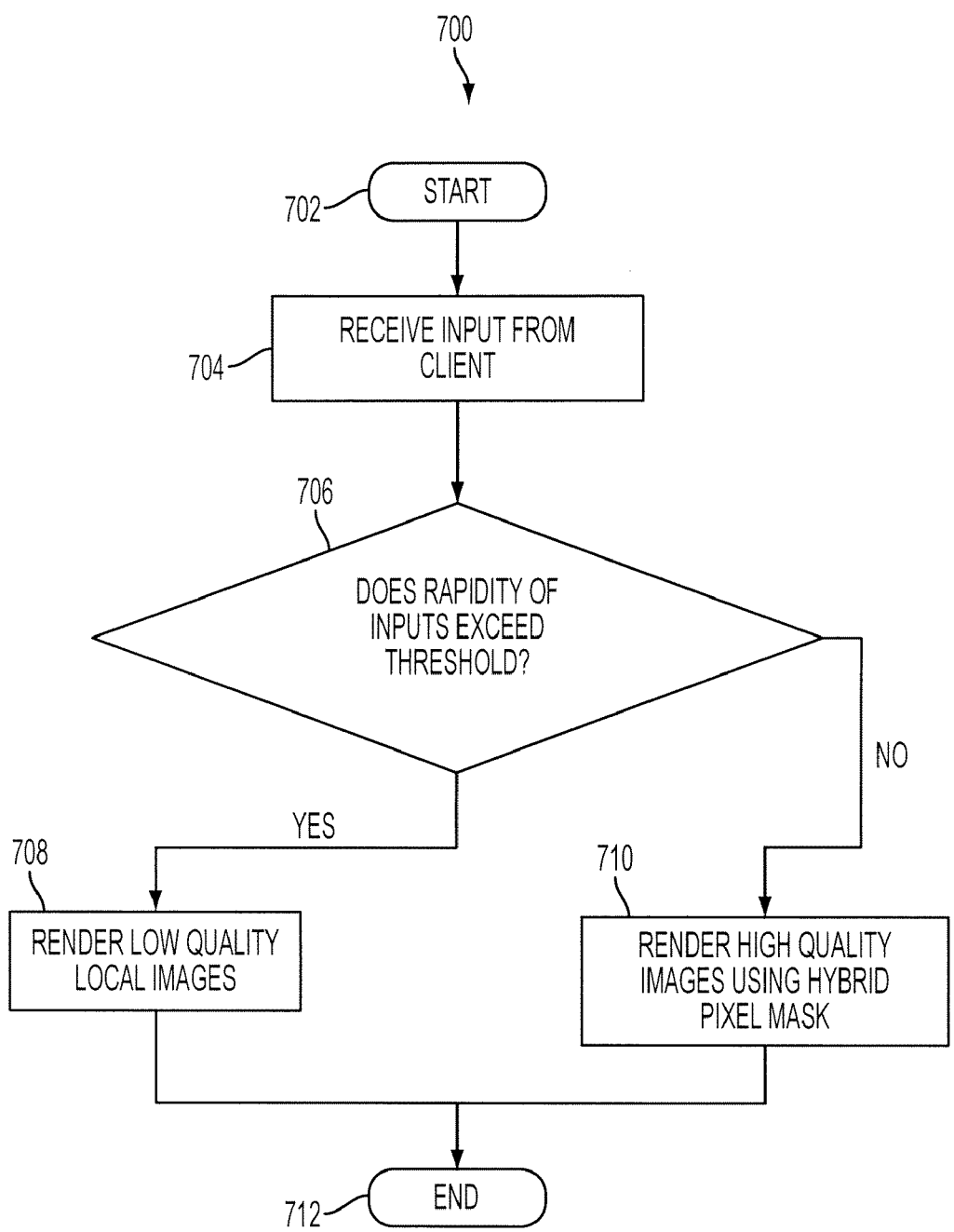
FIG. 7 depicts a flowchart of a method of volume rendering according to an embodiment of the present invention.

FIG. 7 depicts a flowchart of a method 700 of volume rendering according to an embodiment of the present invention. Method 700 may be implemented by any appropriate combination of components of volume rendering system 100. The method begins at step 702.

In step 704, client 106 receives input from a user. In some embodiments, the input may be from a UI, as discussed above, or may be from an I/O device as discussed below with respect to FIG. 8.

In step 706, a determination is made as to the rapidity of inputs received from a user regarding an image at client 106. In some cases, a user is interacting with viewing parameters (e.g., orientation, rotation, etc. in a UI) of an image in a sufficiently rapid fashion (e.g., moving the mouse rapidly) that it would not be reasonable for the user to perceive noticeable changes to the quality of the image being interacted with. In some embodiments, the rapidity of inputs may be determined based on predetermined parameters. Exemplary parameters include a desired interactive frame rate and a delta distance interval traveled during a mouse movement.

If the rapidity of inputs received from a user regarding an image at client 106 exceeds a certain level, the method passes control to step 708 and images are rendered as low-quality local images, as is known. That is, volume rendering system 100 reverts to conventional methods of rendering volumes. For example, if the local rendering frame rate at a client 106 falls below a specified speed or if an indication of mouse movement exceeds a defined threshold, the volume rendering system 100 switches to low-quality local rendering in step 708 using the low-quality sub-sampled volume on the client 106.

If the rapidity of inputs received from a user regarding an image at client 106 does not exceed a certain level, the method passes control to step 710 and a volume is rendered using various steps of method 200, as described above. That is, if a user is interacting with the viewing parameters of an image at client 106 in a slow to moderately fast fashion (e.g., moving the mouse by a small distance) such that moving details can be easily discerned and therefore it is important to view full diagnostic quality images, volume rendering using a pixel mask or a hybrid pixel mask as described above with respect to method 200 is employed.

The method ends at step 712.

Method 700 may be used in embodiments of volume rendering system 100 that use a multi-window display at client 106 in which the interaction with an MPR plane in one window is synchronized with other two MPR planes in other windows. A user may interact within one window by dragging lines that represent the intersection between a selected MPR plane and two other MPR planes. The interactive motion of such lines causes the other two windows to be re-rendered. Depending on the amount each intersection line has been moved, the volume rendering system 100 may be required to render the corresponding MPR windows using either low-quality or high-quality rendering, based on configuration settings for desired interactive frame rate and delta interval of mouse motion as described above with respect to step 706 of method 700.

In an alternative embodiment, volume rendering system 100 always uses local low-quality rendering during interaction as discussed in step 708 of method 700 and high quality rendering as described above with respect to method 200 and step 710 of method 700 is used as a final high-quality update when the interaction stops.

In the same or alternative embodiments, the volume data is not limited to a single 3D volume, but may use a 4D sequence of multiple 3D volumes (e.g., a sequence of volumes representing sequential cardiac phases). In these embodiments, a client 106 automatically triggers, at specific time intervals, the rendering of one of the volumes in the 4D sequence and method 200 is used for the remote client-server visualization of each 3D volume in the sequence. This requires a sub-sampled copy of every volume in the sequence to be transferred to the client 106 as a one-time first step before the sequence is rendered.

Though discussed above generally as a "hybrid pixel mask" or a "pixel mask," it may be understood that a pixel mask may, in some embodiments, not be a hybrid combination of pixel flags and high-quality pixel values, but a result of an XOR operation between the high-quality and low-quality images computed on processing server 104. Once the pixel mask is transferred to the client 106, the client 106 renders all the pixels of a low-quality image locally based on the local copy of the low resolution sub-sampled volume and then performs an XOR operation between the pixel mask and the low-quality image, thereby recovering a high-quality image.

Figure 8:
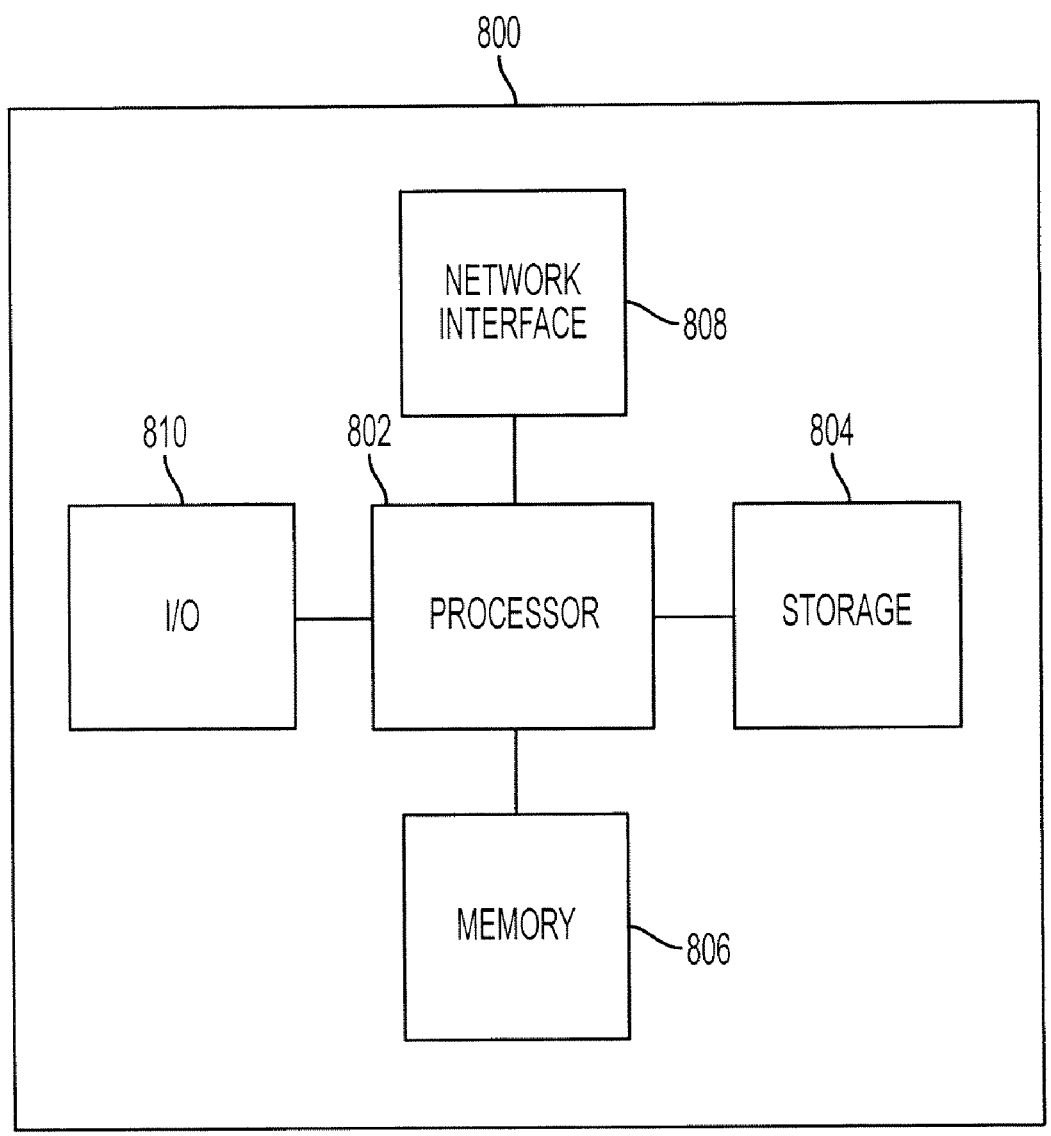
FIG. 8 is a schematic drawing of a controller.

FIG. 8 is a schematic drawing of a computer 800 according to an embodiment of the invention. As discussed above, one or more of the processing server 104 and/or clients 106a-n may be implemented as a computer such as computer 800 and/or may utilize various components of computer 800 as appropriate. Computer 800 contains a processor 802 which controls the overall operation of the computer 800 by executing computer program instructions which define such operation. The computer program instructions may be stored in a storage device 804 (e.g., magnetic disk, database, etc.) and loaded into memory 806 when execution of the computer program instructions is desired. Thus, applications for performing the herein-described method steps, such as volume rendering, in methods 200 and 700 are defined by the computer program instructions stored in the memory 806 and/or storage 804 and controlled by the processor 802 executing the computer program instructions. The computer 800 may also include one or more network interfaces 808 for communicating with other devices via a network (e.g., a peer to peer network, etc.). The computer 800 also includes input/output devices 810 (e.g., display, keyboard, mouse, speakers, buttons, etc.) that enable user interaction with the computer 800. Computer 800 and/or processor 802 may include one or more central processing units, read only memory (ROM) devices and/or random access memory (RAM) devices. One skilled in the art will recognize that an implementation of an actual controller could contain other components as well, and that the controller of FIG. 8 is a high level representation of some of the components of such a controller for illustrative purposes.

According to some embodiments of the present invention, instructions of a program (e.g., controller software) may be read into memory 806, such as from a ROM device to a RAM device or from a LAN adapter to a RAM device. Execution of sequences of the instructions in the program may cause the computer 800 to perform one or more of the method steps described herein, such as those described above with respect to methods 200 and 700. In alternative embodiments, hard-wired circuitry or integrated circuits may be used in place of, or in combination with, software instructions for implementation of the processes of the present invention. Thus, embodiments of the present invention are not limited to any specific combination of hardware, firmware, and/or software. The memory 806 may store the software for the computer 800, which may be adapted to execute the software program and thereby operate in accordance with the present invention and particularly in accordance with the methods described in detail above. However, it would be understood by one of ordinary skill in the art that the invention as described herein could be implemented in many different ways using a wide range of programming techniques as well as general purpose hardware sub-systems or dedicated controllers.

Such programs may be stored in a compressed, uncompiled and/or encrypted format. The programs furthermore may include program elements that may be generally useful, such as an operating system, a database management system, and device drivers for allowing the controller to interface with computer peripheral devices, and other equipment/components. Appropriate general purpose program elements are known to those skilled in the art, and need not be described in detail herein.

Described above is a method of volume rendering using a "smart" client method that has all the advantages of hybrid local and remote rendering, but none of the drawbacks of conventional smart client and thin client methods. Accordingly, the volume rendering system 100 can visualize volume rendered images of full diagnostic quality during interaction. This offers improvement over prior art methods described above in which the system visualizes low-quality rendered images based on a sub-sampled volume during user interaction. The methods described herein do not require the client 106 to compute all the pixels values of a locally rendered image in contrast to the prior art, particularly Engel, where a complete image has to be rendered using the local sub-sampled volume. Further, the present method does not require the processing server 104 to transmit to the client 106 all the pixels of a diagnostic-quality volume rendered image. In prior art methods, such as those described in Saito, the server renders and transmits an entire image to the client. Additionally, the present methods use a pixel mask generated on the processing server 104 and transmitted to the client 106, such that the client 106 has the necessary information to selectively render only a reduced number of pixels locally without requiring a complete reference image existing at the client. Because a smaller amount of information is transmitted to the client 106, network traffic may be reduced, lowering bandwidth use costs. This is in contrast to the prior art discussed above in which the difference between a reference image and a new image is encoded on the processing server 104 and transmitted to the client 106, and then the difference data is decoded and subtracted from a reference image present on the client 106 in order to compute a new image.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method of volume rendering comprising:
   receiving a data loading request from a client;
   loading a full resolution volume dataset on a server;
   computing a low resolution sub-sampled copy of the full resolution volume dataset;
   transmitting the sub-sampled copy of the full resolution volume dataset to the client;
   receiving a rendering request from the client;
   rendering a high quality image from the full resolution volume dataset on the server based at least in part on predetermined rendering parameters specified by the client;
   rendering on the server a low quality image from the low resolution sub-sampled copy of the full resolution volume dataset;
   generating a pixel mask based at least in part on the high quality image and the low quality image on the server; and
   transmitting the pixel mask from the server to the client.

2. The method of claim 1 further comprising:
   receiving the pixel mask from the server at the client;
   rendering an image of a local low resolution sub-sampled volume based on pixel values in the pixel mask; and
   combining the pixel mask values in the pixel mask with selectively rendered pixel values into a high quality image.

3. The method of claim 1 wherein the pixel mask is a hybrid pixel mask.

4. The method of claim 3 wherein generating the hybrid pixel mask comprises:
   performing a XOR operation between the high quality image and the low quality image;
   storing zero values resulting from the XOR operation; and
   replacing non-zero values resulting from the XOR operation with pixel values from the high quality image.

5. The method of claim 2, wherein the pixel mask is a hybrid pixel mask and generating the high quality image comprises:
   selectively rendering only pixel values flagged as zero in the pixel mask; and
   combining the selectively rendered pixel values with non-zero values in the pixel mask.

6. The method of claim 1 wherein generating the pixel mask further comprises:
   computing a XOR operation between pixels in the high quality image and low quality image computed on the server.

7. The method of claim 6, further comprising:
   receiving the pixel mask from the server at the client;
   rendering a low quality image of a local low resolution sub-sampled volume;
   combining pixel values of the pixel mask and pixel values of the low quality image using a XOR operator; and
   generating a high quality image based on the combined pixel values.

8. The method of claim 1 wherein transmitting the sub-sampled copy of the full resolution volume from the server to the client comprises compressing the sub-sampled copy of the full resolution volume.

9. The method of claim 1 wherein transmitting the pixel mask from the server to the client comprises compressing the pixel mask using lossless compression.

10. The method of claim 1 wherein the rendering request from the client to the server is based on the rapidity of inputs received from a user interacting with viewing parameters on the client.

11. A system for volume rendering comprising:
    means for receiving a data loading request;
    means for loading a full resolution volume dataset;

means for computing a low resolution sub-sampled copy of the full resolution volume dataset;
means for transmitting the sub-sampled copy of the full resolution volume dataset;
means for receiving a rendering request;
means for rendering a high quality image from the full resolution volume dataset based at least in part on predetermined rendering parameters;
means for rendering a low quality image from the low resolution sub-sampled copy of the full resolution volume dataset;
means for generating a pixel mask based at least in part on the high quality image and the low quality image; and
means for transmitting the pixel mask.

12. The apparatus of claim 11 further comprising:
means for receiving the pixel mask;
means for rendering an image of a local low resolution sub-sampled volume based on pixel values in the pixel mask; and
means for combining the pixel mask values in the pixel mask with selectively rendered pixel values into a high quality image.

13. The apparatus of claim 11 wherein the means for generating the pixel mask comprises:
means for performing a XOR operation between the high quality image and the low quality image;
means for storing zero values resulting from the XOR operation; and
means for replacing non-zero values resulting from the XOR operation with pixel values from the high quality image.

14. The apparatus of claim 12, wherein the pixel mask is a hybrid pixel mask and the means for generating the high quality image comprises:
means for selectively rendering only pixel values flagged as zero in the pixel mask; and
means for combining the selectively rendered pixel values with non-zero values in the pixel mask.

15. The apparatus of claim 11 wherein the means for generating the pixel mask further comprises:
means for computing a XOR operation between pixels in the high quality image and low quality image.

16. The apparatus of claim 15, further comprising:
means for receiving the pixel mask;
means for rendering a low quality image of a local low resolution sub-sampled volume;
means for combining pixel values of the pixel mask and pixel values of the low quality image using a XOR operator; and
means for generating a high quality image based on the combined pixel values.

17. The apparatus of claim 11 further comprising:
means for compressing the sub-sampled copy of the full resolution volume.

18. A non-transitory machine readable medium having program instructions stored thereon, the instructions capable of execution by a processor and defining the steps of:
receiving a data loading request from a client;
loading a full resolution volume dataset on a server;
computing a low resolution sub-sampled copy of the full resolution volume dataset;
transmitting the sub-sampled copy of the full resolution volume dataset to the client;
receiving a rendering request from the client;
rendering a high quality image from the full resolution volume dataset on the server based at least in part on predetermined rendering parameters specified by the client;
rendering on the server a low quality image from the low resolution sub-sampled copy of the full resolution volume dataset;
generating a pixel mask based at least in part on the high quality image and the low quality image on the server; and
transmitting the pixel mask from the server to the client.

19. The machine readable medium of claim 18 wherein the instructions further define the steps of:
receiving the pixel mask from the server at the client;
rendering an image of a local low resolution sub-sampled volume based on pixel values in the pixel mask; and
combining the pixel mask values in the pixel mask with selectively rendered pixel values into a high quality image.

20. The machine readable medium of claim 19 wherein the instructions for generating the pixel mask further define the steps of:
performing a XOR operation between the high quality image and the low quality image;
storing zero values resulting from the XOR operation; and
replacing non-zero values resulting from the XOR operation with pixel values from the high quality image.

21. The machine readable medium of claim 18, wherein the pixel mask is a hybrid pixel mask and the instructions for generating the high quality image further define the steps of:
selectively rendering only pixel values flagged as zero in the pixel mask; and
combining the selectively rendered pixel values with non-zero values in the pixel mask.

22. The machine readable medium of claim 18 wherein the instructions for generating the pixel mask further define the step of:
computing a XOR operation between pixels in the high quality and low quality images computed on the server.

23. The machine readable medium of claim 22, wherein the instructions further define the steps of:
receiving the pixel mask from the server at the client;
rendering a low quality image of a local low resolution sub-sampled volume;
combining pixel values of the pixel mask and pixel values of the low quality image using a XOR operator; and
generating a high quality image based on the combined pixel values.

* * * * *